US011938347B2

(12) United States Patent
Kamenko

(10) Patent No.: US 11,938,347 B2
(45) Date of Patent: Mar. 26, 2024

(54) ULTRASOUND APPARATUS FOR MECHANICALLY APPLYING ULTRASOUND WAVES EFFICIENTLY

(71) Applicant: SONNEXT LTD., Beit Zait (IL)

(72) Inventor: Vyacheslav Kamenko, Beit Zait (IL)

(73) Assignee: SONNEXT LTD., Beit Zait (IL)

( * ) Notice: Subject to any disclaimer, the term of this patent is extended or adjusted under 35 U.S.C. 154(b) by 892 days.

(21) Appl. No.: 16/970,297

(22) PCT Filed: Feb. 15, 2019

(86) PCT No.: PCT/IL2019/050185
§ 371 (c)(1),
(2) Date: Aug. 14, 2020

(87) PCT Pub. No.: WO2019/159175
PCT Pub. Date: Aug. 22, 2019

(65) Prior Publication Data
US 2023/0096237 A1    Mar. 30, 2023

Related U.S. Application Data

(60) Provisional application No. 62/631,649, filed on Feb. 17, 2018.

(51) Int. Cl.
*A61N 7/00*            (2006.01)
(52) U.S. Cl.
CPC ........ *A61N 7/00* (2013.01); *A61N 2007/0004* (2013.01)
(58) Field of Classification Search
CPC .......................... A61N 7/00; A61N 2007/0004
See application file for complete search history.

(56) References Cited

U.S. PATENT DOCUMENTS

| 4,517,985 | A  | 5/1985 | Teslawski et al. |
| 5,520,612 | A  | 5/1996 | Winder et al. |
| 6,425,870 | B1 | 7/2002 | Flesch |
| 8,366,622 | B2 | 2/2013 | Slayton et al. |
| 8,506,486 | B2 | 8/2013 | Slayton et al. |
| 10,369,386 | B2 | 8/2019 | Van Heesch et al. |
| 11,717,707 | B2 | 8/2023 | Slayton et al. |
| 2008/0214937 | A1 | 9/2008 | Kim |

(Continued)

FOREIGN PATENT DOCUMENTS

| DE | 3227624 A1 | 1/1984 |
| JP | H08187265 A | 7/1996 |
| JP | 2011522625 A | 8/2011 |

(Continued)

OTHER PUBLICATIONS

International Search Report dated May 19, 2019 issued in corresponding PCT/IL2019/050185 application (2 pages).

*Primary Examiner* — Jason M Ip
(74) *Attorney, Agent, or Firm* — Millen, White, Zelano & Branigan P.C.; William F. Nixon

(57) ABSTRACT

The present invention relates to an ultrasound apparatus for efficiently applying ultrasound waves over a treated area by mechanically moving the ultrasound transducer over an area larger than the Effective Radiating Area (ERA) comprising: (a) an ultrasound transducer, connected by wiring, for dispersing ultrasound waves; (b) an electric actuator for spinning a crank, wherein a shaft is eccentrically attached to said crank for rotatably whirling said transducer in circles.

8 Claims, 4 Drawing Sheets

(56) References Cited

U.S. PATENT DOCUMENTS

2011/0112405 A1  5/2011  Barthe et al.
2015/0297182 A1  10/2015  Peng et al.

FOREIGN PATENT DOCUMENTS

| KR | 20030080507 A | 10/2003 |
|----|---------------|---------|
| KR | 101824462 B1  | 2/2018  |
| RU | 2547180 C2    | 4/2015  |
| RU | 2589614 C2    | 7/2016  |
| WO | 2009149390 A1 | 12/2009 |

ULTRASOUND APPARATUS FOR MECHANICALLY APPLYING ULTRASOUND WAVES EFFICIENTLY

TECHNICAL FIELD

The present invention relates to cosmetic treatment apparatuses. More particularly, to an ultrasound apparatus used in various treatment applications.

BACKGROUND

As of today, ultrasound is widely used in medicine, cosmetics, body shaping, wound treatment, pain relief, blood flow stimulation, skin treatments and spa therapy. Ultrasound waves are applied to a human body via a hand-held device or a stationary, fixed positioned device, directly touching the treated area of the human body. What is needed is a convenient, easy to use, and comfortable means for applying the ultrasound waves efficiently.

US2015297182 discloses a mechanically rotating intravascular ultrasound probe. The publication discloses a forward-looking mechanically rotating intravascular ultrasound probe having a small volume, a high image resolution and good imaging stability. The intravascular ultrasound probe includes a catheter, an ultrasonic transducer disposed at a front end of a cavity of the catheter and a driving apparatus that drives the ultrasonic transducer to rotate mechanically. The driving apparatus is a micro motor disposed in the cavity of the catheter, including a rotor and a stator. The ultrasonic transducer is installed on top of the rotor and electrically connected to the rotor, and the rotor is also electrically connected to the stator. The catheter is a magnetic metal tube, and a front end thereof is enclosed by an acoustic window which has a spherical tip and allows ultrasonic waves of the ultrasonic transducer to pass through. The acoustic window is filled with an ionic liquid having a function of an ultrasonic coupling agent. The ultrasound probe solves a problem of rotation torsion of an image when the catheter passes through a lesion with high-grade stenosis or a curved blood vessel section, and achieves forward scanning imaging and side scanning imaging for a blood vessel wall. However, the described probe is limited to the rotation around its own axle. As well the ionic liquid playing a role of the second conductor is limiting the power specs and type of application of the above described transducer.

As a therapeutic ultrasound requires power specs up to 1000 times higher of a diagnostic ultrasound, it would therefore be desired to propose a system void of these deficiencies.

SUMMARY

It is an object of the present invention to provide an ultrasound apparatus for applying the ultrasound waves efficiently.

It is another object of the present invention to provide a non-surgical ultrasound apparatus, that applies the ultrasound waves easily, automatically, and safely to the patient.

It is still another object of the present invention to provide an automatic ultrasound apparatus, for cosmetic treatment.

Other objects and advantages of the invention will become apparent as the description proceeds.

The present invention relates to an ultrasound apparatus for efficiently applying ultrasound waves over a treated area by mechanically moving the ultrasound transducer comprising: (a) an ultrasound transducer, connected by wiring, for dispersing ultrasound waves; (b) a shaft for holding said transducer; (c) an electric actuator for spinning a crank, wherein said shaft is eccentrically attached to said crank for rotatably whirling said transducer in circles; (d) a stabilizer, for leading said wiring of said ultrasound transducer, and for holding said shaft in an angle for reducing the twisting of said wiring, of said ultrasound transducer, when said actuator whirls said transducer; (e) a first linear bearing for guiding the bottom part of said stabilizer while said bottom part of the stabilizer slides up and down; and (f) a control unit, logically connected to said electric actuator, capable of receiving instructions, from the user, and capable of controlling the whirling of said ultrasound transducer, by controlling said electric actuator, for performing said instructions.

Preferably, the apparatus further comprises a friction reducer and a second linear bearing for protecting the wiring and guiding it through a rectifying mechanism, when the actuator whirls said transducer.

Preferably, a single cable provides a continuous electrical connection from the input connector of the apparatus to the moving ultrasound transducer for making a number of turns without causing damage to said cable.

Preferably, the electric actuator, is driven by an electronic circuitry or by directly applied power, for whirling the ultrasound transducer in at least one motion type such as circular motion, linear motion, angular motion, spin motion, vibration, in at least one direction or combination of said directions and motion type patterns.

Preferably, the apparatus further comprises a connector having at least one BNC connectors for connecting to said ultrasound apparatus, where the whole connector assembly, including non-BNC type of contacts are held in place by utilizing the BNC locking mechanism.

Preferably, the apparatus may be embodied in a stand-alone device or may be incorporated into a larger more comprehensive machinery.

In one embodiment, the apparatus further comprising a coupler implemented for changing speed, pattern, torque or amplitude of the motion of the ultrasound transducer In one embodiment, the ultrasound transducer is directly attached to said electric actuator.

In one embodiment, the apparatus is used to avoid burns caused by the high-power ultrasound applied for a longer than necessary time to the same spot of the treated area.

In one embodiment, the electrically driven ultrasound transducer is used to increase the blood flow in the treated area due to ability to perform motions at the speed amplitude and pattern impossible to perform manually.

In one embodiment, the electrically driven ultrasound transducer moves in certain types of motions, that generate its own low frequency waves, which in coherence with the main ultrasound carrier frequency produces more effective and more penetrative pulses not producible by a single frequency source In one embodiment, the electrically driven ultrasound transducer reduces the hardship of the manual motion during the treatment process.

BRIEF DESCRIPTION OF THE DRAWINGS

The accompanying drawings, and specific references to their details, are herein used, by way of example only, to illustratively describe some of the embodiments of the invention.

In the drawings.

DETAILED DESCRIPTION

The terms of "front", "rear", "down", "up", "bottom", "upper", "horizontal", "vertical", "right", "left" or any reference to sides or directions are used throughout the description for the sake of brevity alone and are relative terms only and not intended to require a particular component orientation.

As known in the art, ultrasound waves may be used in wound treatment, ulcer treatment, pain relief, blood flow stimulation, body shaping, fat reduction, cellulite reduction, skin treatment and other applications for cosmetic or medical treatment. Ultrasound waves may be applied to the patient via a hand-held device or a stationary, fixed positioned device, by directly touching the skin of the treated area of the body. However, the Effective Radiating Area (ERA) of the ultrasound transducer is very slim. Thus, in order to apply an equal amount of energy to an area larger than the ERA of the ultrasound transducer the transducer needs to be moved within a constant speed throughout the treated area. Furthermore, due to the conical shape of the ultrasound beam, the focus zone of the ultrasound beam is typically narrower than the transducer's ERA, which requires a great amount of motion, to the transducer, in order to be effective, even when the treated area is fairly small. Not to mention that when high-power ultrasound waves are applied, over time, to the same area, the absorption of the waves may cause that body part to heat, and burn. The present invention introduces an ultrasound apparatus for efficiently applying ultrasound waves over an area larger than the ERA of an ultrasound transducer, by driving by an electric actuator, which whirls the ultrasound transducer, for dispersing the ultrasound waves over an area larger than the ERA of an ultrasound transducer thus protecting the client from harm.

Figure 1:
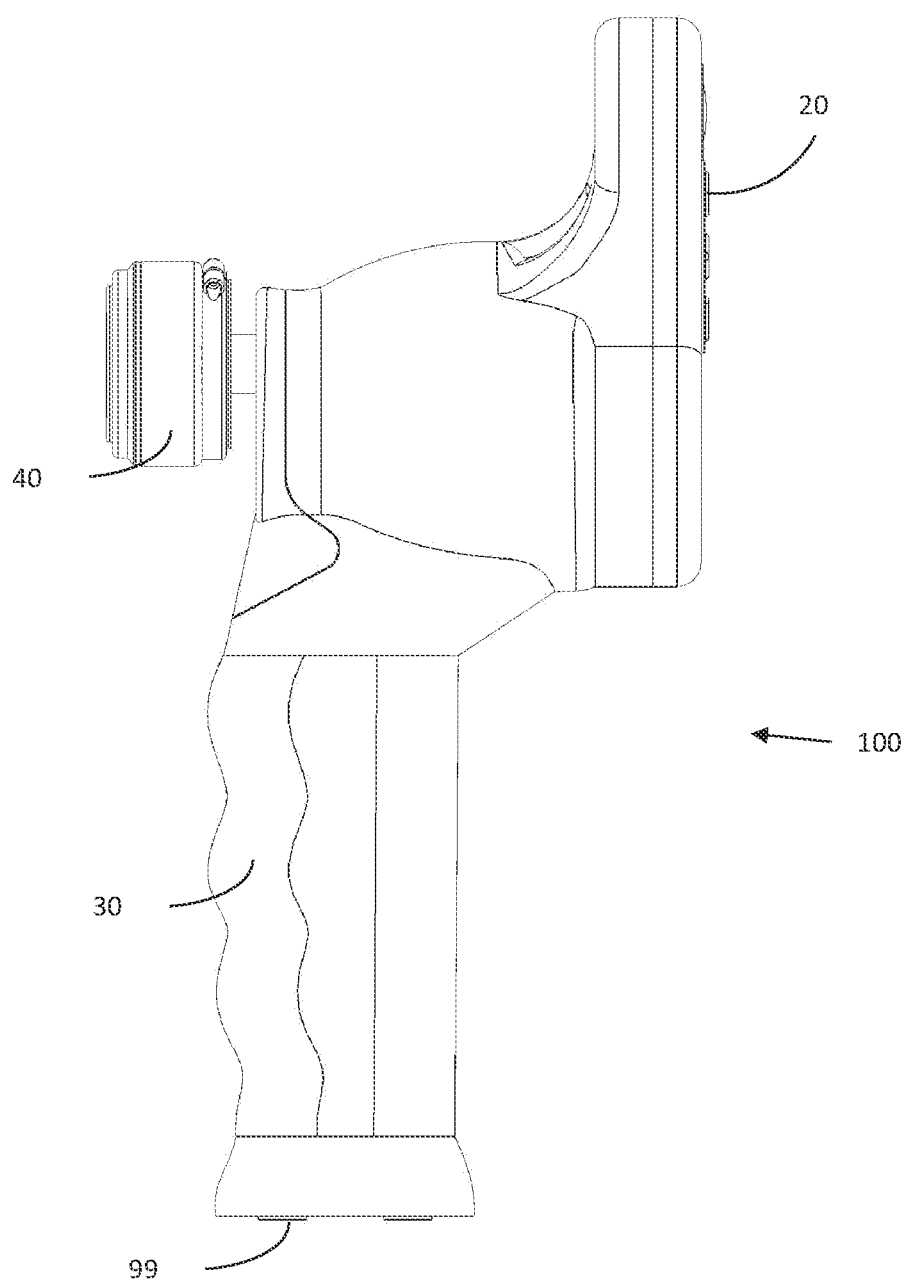
FIG. 1 is a diagram of a hand-held ultrasound apparatus for applying the ultrasound waves efficiently, according to an embodiment of the invention.

FIG. 1 is a diagram of a hand-held ultrasound apparatus for applying the ultrasound waves efficiently, according to an embodiment of the invention. The apparatus 100 may be a hand-held ultrasound apparatus having a transducer 40 that may be whirled. The transducer 40 may be whirled by an electric actuator, such as described in relation to FIG. 2, for example. When the operator holds the ultrasound apparatus, by gripping the handle 30, and aims the transducer 40 to the body of the patient the ultrasound transducer may be whirled, in circles, while applying the ultrasound waves. Thus, the transducer 40 efficiently disperses the ultrasound waves over an area larger than the transducer's initial ERA.

One of the features of the described apparatus is to provide a continuous electrical connectivity to the ultrasound transducer 40 while allowing it to make an endless number of turns in a circular pattern without excessive distortion of the electrical conductor. Before being converted to an ultrasound vibration, by the ultrasound transducer, the driving electrical signal is usually formed as an RF signal of a high power, as therapeutic ultrasound may require up to tens of Watts to be applied. Thus, the conduction of such a signal presents an additional problem caused by the nature of the RF cables, which require undisturbed coaxiality of the conductors within. The implementation of the sliding contacts may pose an engineering challenge in terms of cost and reliability.

The simplest and the most reliable way would be utilization of the basic cable without any additional contacts. The following mechanism description enables a single cable connectivity between the fixed input end, e.g. connection point 99 in FIG. 1, and the moving end, e.g. the transducer 40, where the parameters of distortion of the cable could be calculated and adjusted as required.

Figure 2:
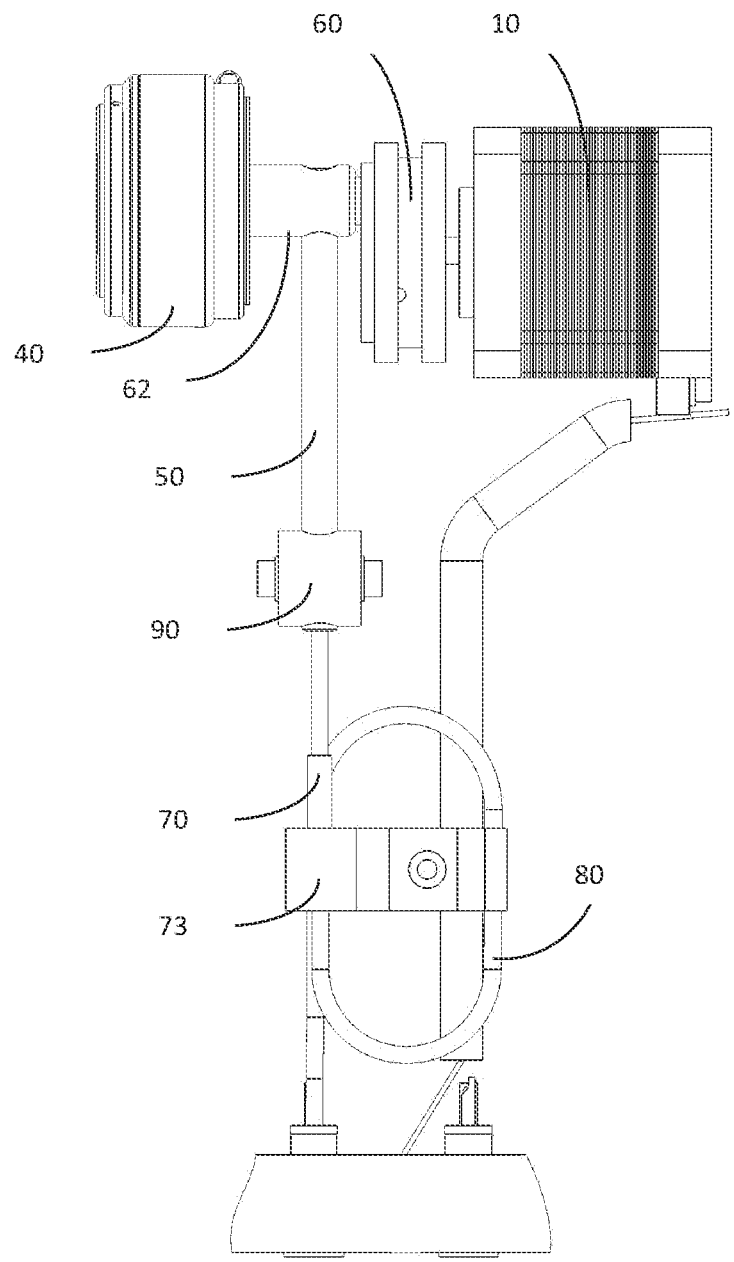
FIG. 2 is a diagram of some of the inner parts of the ultrasound apparatus, according to an embodiment of the invention.

FIG. 2 is a diagram of some of the inner parts of the ultrasound apparatus, according to an embodiment of the invention. The ultrasound transducer 40, as described in relations to FIG. 1, may have a stainless-steel cover with a PZT807 piezoelectric crystal, or any other ultrasound transducer capable of directing ultrasound waves for human treatment. The ultrasound transducer 40 may be connected by wiring. The wiring may be an RF cable or any other wiring capable of transferring the electric signals to the transducer 40. The ultrasound transducer 40 may be whirled by the electric actuator 10. The actuator 10 may be an electric motor, e.g. brush or brushless, a stepper motor, or servo motor, solenoid, an angular actuator or a linear actuator, such as the Nema 17 Stepper Motor, or any other actuator capable of whirling the transducer. In one embodiment, the actuator 10 may whirl the transducer 40 in a circular pattern in any direction or in any other angular pattern. In an embodiment, the actuator 10 may whirl the transducer 40 in one direction and then switch the direction of rotation of the actuator 10 before completing the whole circle. In other embodiments, the actuator 10 may vibrate the transducer by rapidly changing the actuators direction of rotation. Combinations of the vibrations and rotations are also possible according to other embodiments.

In one embodiment, the actuator 10, as depicted in FIG. 2, may spin a crank 60, where the crank 60 has a shaft 62 which is attached pivotally and eccentrically, for rotatably whirling the transducer 40. The transducer 40 may be attached to the shaft 62. Thus, when the actuator 10 spins, the crank 60 may spin as well with its eccentrically placed shaft 62 making circular movements, which whirls the transducer 40 in circles. When the actuator's shaft 62 spins, it may commit a circular motion around the actuator's 10 center axis which may whirl the transducer in the same circular pattern. This will allow the transducer 40 to be whirled in circular pattern in any direction or any other angular pattern by switching direction of rotation of the actuator 10 before completing the whole circle, or vibrate, by rapidly changing the actuator's direction of rotation. In one embodiment, combination of the vibration and rotation is possible as well. In one embodiment, the proper displacement of axes, i.e. the axis of the shaft 62 and the axis of the actuator will allow to move the transducer in a circular pattern without overlapping the ultrasound beam focus zone, thus increasing the equality of the energy applied to the whole treated area.

The apparatus 100, of FIG. 2, may also have a stabilizer 50 which may be used to stabilize the angle of the transducer 40, when the actuator 10 spins and whirls the transducer 40. The stabilizer 50 may be a hollow tube made of metal, or any other rigid material, for leading the wiring of the ultrasound transducer 40. In one embodiment the top part of stabilizer 50 is inserted into the shaft 62 and attached within the shaft 62. When the shaft 62 moves the transducer 40, the stabilizer 50 may hold the shaft, and the transducer 40, in the position normal to the first linear bearing 90 which guides the stabilizer 50 at the bottom, thus reducing the twisting of the wiring which is attached to the ultrasound transducer 40. The first linear bearing 90 is held within the apparatus cover by its axis 95 thus said bearing is capable of committing an angular movement around said axis 95. While the stabilizer 50, at its top side, repeats the circular motions committed by the shaft 62, the angular movement of the bearing 90, which holds the bottom side of stabilizer 50, may have a much lower amplitude of the angular movement.

In one embodiment, a friction reducer 70, as depicted in FIG. 2, may be used for protecting the movement of wiring 80. The friction reducer 70, i.e. linear guide, may be a hollow tube made of metal, or any other rigid material, for leading the wiring of the ultrasound transducer 40. In one embodiment, the friction reducer 70 may be movably held, by a second linear bearing 73. Thus, the wiring 80 may be protected in the friction reducer 70 while the friction reducer 70 slides up and down, inside the second linear bearing 73, with the movement of the transducer 40.

Figure 3:
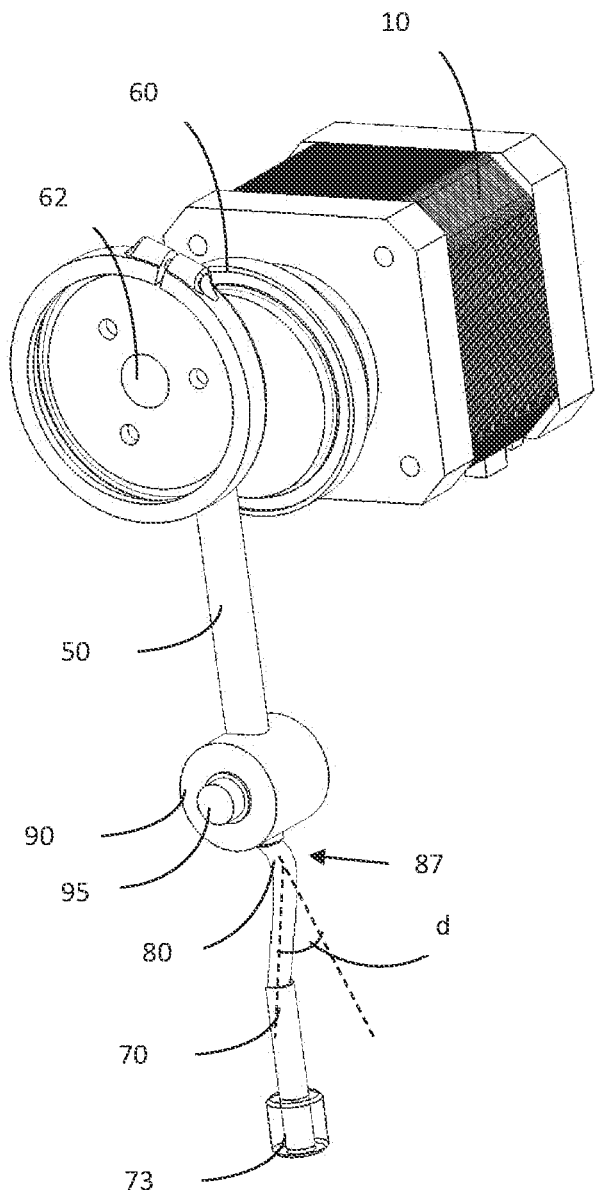
FIG. 3 is a diagram of an isometric view of some of the inner parts of the ultrasound apparatus, according to an embodiment of the invention.

FIG. 3 is a diagram of an isometric view of some of the inner parts of the ultrasound apparatus, according to an embodiment of the invention. As described in relations to FIG. 2, the transducer cable 80 may run through a stabilizer 50 and may further run through the hollow shaft 62, to which the transducer is attached. The stabilizer 50 may be inserted into the first linear bearing 90 which may be able to turn around its axis 95 within the apparatus covering. The first linear bearing 90 may act as a guide for the stabilizer 50, as well as serving a purpose of the first stage rectifier of the cable distortion. As shown in the FIG. 3 the maximum distortion angle 'cl' of the cable would be defined by the equation tan(d)=Movement Radius of the shaft 62 (MR)/Length between the axis of the actuator and the axis 95 of the first linear bearing (LF). By the adjustment of the MR and LF the desired maximum cable distortion angle could be achieved. While the first linear bearing 90 reduces the cable's left/right motion in the X direction caused by the X and Y movement path, the second linear bearing 73 limits the cable's up/down motion to the Y direction only. In the second stage rectification of the cable movement in the Y direction is handled. The friction reducer 70 encloses the cable on the contact surface with the second linear bearing 73 thus minimizing the friction and protecting the cable. The distance between the two linear bearings, 90 and 73, can affect the cable Distortion Radius 87—by increasing the distance the radius will increase as well.

Beyond the friction reducer 70, the cable 80 may be freely folded in a 180 degrees arc, with a desired radius up to a fixing point within the apparatus embodiment, as depicted in FIG. 2. With the cable movements in the Y direction the arc may keep its radius, while its center displacement may be equal to the half of the cable Y direction motion amplitude.

Returning to FIG. 1, the apparatus 100 may have a control unit capable of receiving instructions such as by user interface 20. The user interface 20 may have buttons, levers, screen, touch screen or any other user interface components. The control unit, which may also be logically connected to the electric actuator, may be capable of controlling the rotation of the ultrasound transducer, by controlling the electric actuator, for performing the received instructions from the user. The control unit may also be capable of controlling speed and angular amplitude of the transducer 40 in different manners for creating different massaging motion types. In one embodiment, in order to allow the proper displacement of axes, the control unit may control the transducer to move in a circular pattern without overlapping the ultrasound beam focus zone, thus increasing the equality of the energy applied to the whole treated area.

In one embodiment the ultrasound apparatus may also comprise an electronic circuitry to allow user to control the motion's speed, the amplitude and/or the pattern of the ultrasound waves of the transducer. In an embodiment, the actuator may be driven directly by applying electricity to the electric actuator.

The described ultrasound apparatus may help to reduce the hardship of the manual motion during the treatment process used today. As described above, the use of the ultrasound apparatus may provide a more equal energy dispersion to the whole treated area in comparison to the manual moved transducer used today.

In one embodiment the ultrasound apparatus may be used to increase the blood flow in the treated area due to ability to perform motions at the speed amplitude and pattern. In one embodiment the ultrasound apparatus may whirl the ultrasound transducer in certain types of motions, such as vibration or other, and it may generate its own low frequency waves which in coherence with the main ultrasound carrier frequency may produce more effective and more penetrative pulses not producible by a single frequency source.

In one embodiment, the ultrasound apparatus may have a coupler or a coupler mechanism such as gearbox, lever, camshaft or any other mechanism used for changing speed, pattern, torque or amplitude of motion of the ultrasound transducer whirled by the actuator. Alternatively, the ultrasound transducer may be directly attached to the electric actuator.

In one embodiment, the electric actuator, of the ultrasound apparatus, may be driven by an electronic circuitry or by directly applied power, for whirling the ultrasound transducer in at least one motion type such as circular motion, linear motion, angular motion, spin motion, vibration, or other motion type, in at least one direction or combination of different directions and motion types.

Figure 4:
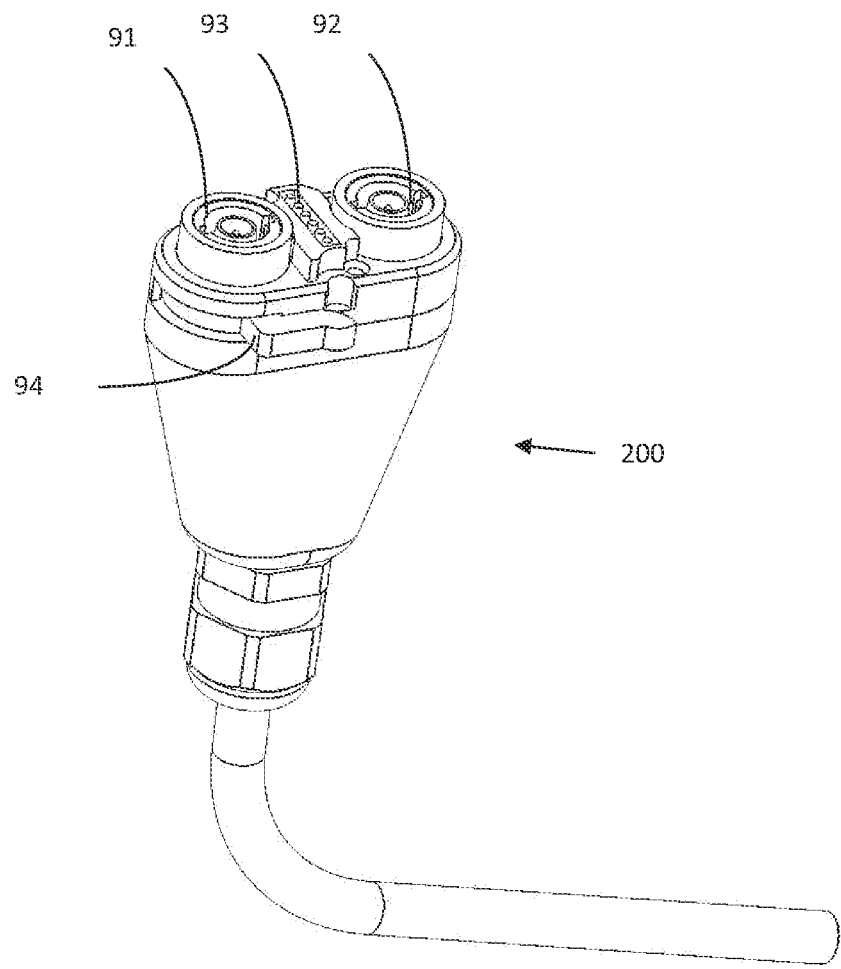
FIG. 4 is a diagram of a connector for the ultrasound apparatus, according to an embodiment of the invention.

FIG. 4 is a diagram of a connector for the ultrasound apparatus, according to an embodiment of the invention. In one embodiment, a connector 200, having two BNC connectors 91-93, may be used for connecting to the ultrasound apparatus. The first BNC connector 91, for example, may be used for connecting the RF signals feeding point to the ultrasound transducer while the second BNC connector 92 may be used for feeding the electricity to the controller and the electric actuator, for example. The connector may also have other contact points 93 for transferring other signals to the ultrasound apparatus. The ultrasound apparatus may have the appropriate connectors at its bottom, such as connecting point 99 depicted in FIG. 1, for receiving the connector 200. In one embodiment a lever, such as lever 94, may be attached to each of the BNC connectors for easy lock of the connector to the ultrasound apparatus. Thus, the connector 200 may be attached to the bottom of ultrasound apparatus 100 and the levers may be turned in order to lock the cables feeding the ultrasound apparatus 100. Thus, the whole connector assembly 200 may be reliably attached and fastened utilizing the effective BNC locking mechanism.

While the above description discloses many embodiments and specifications of the invention, these were described by way of illustration and should not be construed as limitations on the scope of the invention. The described invention may be carried into practice with many modifications which are within the scope of the appended claims.

The invention claimed is:

1. An ultrasound apparatus for applying ultrasound waves over a treated area by mechanically moving the ultrasound transducer comprising:
    an ultrasound transducer, connected by wiring, for dispersing ultrasound waves;
    a shaft for holding said transducer;
    an electric actuator for spinning a crank, wherein said shaft is eccentrically attached to said crank for rotatably whirling said transducer in circles;
    a stabilizer, attached to said shaft for leading said wiring of said ultrasound transducer, and for holding said shaft, when said actuator whirls said transducer;
    a first linear bearing for guiding said stabilizer while said stabilizer slides up and down in said first linear bearing, wherein said stabilizer holds said shaft in the position normal to said first linear bearing for reducing the twisting of said wiring, of said ultrasound transducer, when said actuator whirls said transducer; and
    a control unit, logically connected to said electric actuator, for receiving instructions, from the user, and for controlling the whirling of said ultrasound transducer, by controlling said electric actuator, for performing said instructions.

2. An apparatus according to claim 1, further comprising a friction reducer and a second linear bearing for protecting the wiring and guiding it through a rectifying mechanism, when the actuator whirls said transducer.

3. An apparatus according to claim 1, wherein a single cable provides a continuous electrical connection from the input connector of the apparatus to the moving ultrasound transducer for making an endless number of turns.

4. An apparatus according to claim 1, wherein the electric actuator, is driven by an electronic circuitry or by directly applied power, for whirling the ultrasound transducer in at least one motion type such as circular motion, linear motion, vibration, in at least one direction or combination of said directions and motion type patterns.

5. An apparatus according to claim 1, further comprising a connector having at least one BNC connectors for connecting to said ultrasound apparatus, where the whole connector assembly, including non-BNC type of contacts are held in place by utilizing the BNC locking mechanism.

6. An apparatus according to claim 1, where the apparatus may be embodied in a standalone device or may be incorporated into a larger more comprehensive machinery.

7. An apparatus according to claim 1, further comprising a coupler implemented for changing speed, pattern, torque or amplitude of the motion of the ultrasound transducer.

8. An apparatus according to claim 1, where the ultrasound transducer is directly attached to said electric actuator.

* * * * *